US00PP25365P2

(12) United States Plant Patent
Hoogenraad et al.

(10) Patent No.: US PP25,365 P2
(45) Date of Patent: Mar. 24, 2015

(54) ***BERBERIS* PLANT NAMED 'HOHO 2'**

(50) Latin Name: *Berberis thungergii*
Varietal Denomination: Hoho 2

(71) Applicants: Mark Sebastiaan Hoogenraad, Ederveen (NL); Ralph Matheus Hoof, Zevenaar (NL)

(72) Inventors: Mark Sebastiaan Hoogenraad, Ederveen (NL); Ralph Matheus Hoof, Zevenaar (NL)

( * ) Notice: Subject to any disclaimer, the term of this patent is extended or adjusted under 35 U.S.C. 154(b) by 46 days.

(21) Appl. No.: 13/986,426

(22) Filed: May 1, 2013

(51) Int. Cl.
*A01H 5/00* (2006.01)

(52) U.S. Cl.
USPC ..... Plt./241

(58) Field of Classification Search
CPC ..... A01H 5/12; A01H 5/00
USPC ..... Plt./241
See application file for complete search history.

*Primary Examiner* — June Hwu
*Assistant Examiner* — Keith Robinson
(74) *Attorney, Agent, or Firm* — Penny J. Aguirre

(57) ABSTRACT

A new cultivar of *Berberis*, 'Hoho 2', that is characterized by its bright gold foliage, its foliage that is resistant to leaf scorch when grown in warm temperatures and high sun levels, and its compact, low growing (flattened) and broadly spreading plant habit.

2 Drawing Sheets

Botanical classification: *Berberis thungergii*.
Cultivar designation: 'Hoho 2'.

BACKGROUND OF THE INVENTION

The present invention relates to a new and distinct cultivar of *Berberis thungerii*, and will be referred to hereafter by its cultivar name, 'Hoho 2'. 'Hoho 2' is grown for use as a landscape shrub.

The new cultivar was discovered by the Inventors in June of 2010 as a naturally occurring branch mutation of 'Aurea' (not patented) that was growing in a production field in Zevenaar, The Netherlands.

Asexual propagation of the new cultivar was first accomplished by one the Inventors using softwood stem cuttings in Zevenaar, The Netherlands in July of 2011. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar, which in combination distinguish 'Hoho 2' as a new and distinct cultivar of *Berberis*.

1. 'Hoho 2' exhibits bright gold foliage.
2. 'Hoho 2' exhibits foliage that is resistant to leaf scorch when grown in warm temperatures and high sun levels.
3. 'Hoho 2' exhibits a compact, low growing (flattened) and broadly spreading plant habit.

The parent plant, 'Aurea', differs from 'Hoho 2' in having a less compact and more upright plant habit and lighter gold foliage that tends to scorch under high sun levels. 'Hoho 2' can be most compared to the cultivars 'Bogozam' (U.S. Plant Pat. No. 8,215) and 'Monlers' (U.S. Plant Pat. No. 9,577). Both cultivars are similar to 'Hoho 2' in having gold foliage and a compact plant habit. 'Bogozam' differs from 'Hoho 2' in having a mounded and less spreading plant habit and foliage that tends to scorch under high sun levels. 'Monlers' differs from 'Hoho 2' in having a more mounded plant habit and in having longer spines.

BRIEF DESCRIPTION OF THE DRAWINGS

The accompanying colored photographs illustrate the overall appearance and distinct characteristics of the new *Berberis*. The photographs were taken of a plant two-years in age as grown outdoors in a 2-liter container in Zevenaar, The Netherlands.

The photograph in FIG. 1 provides a side view of 'Hoho 2'.

Figure 1:
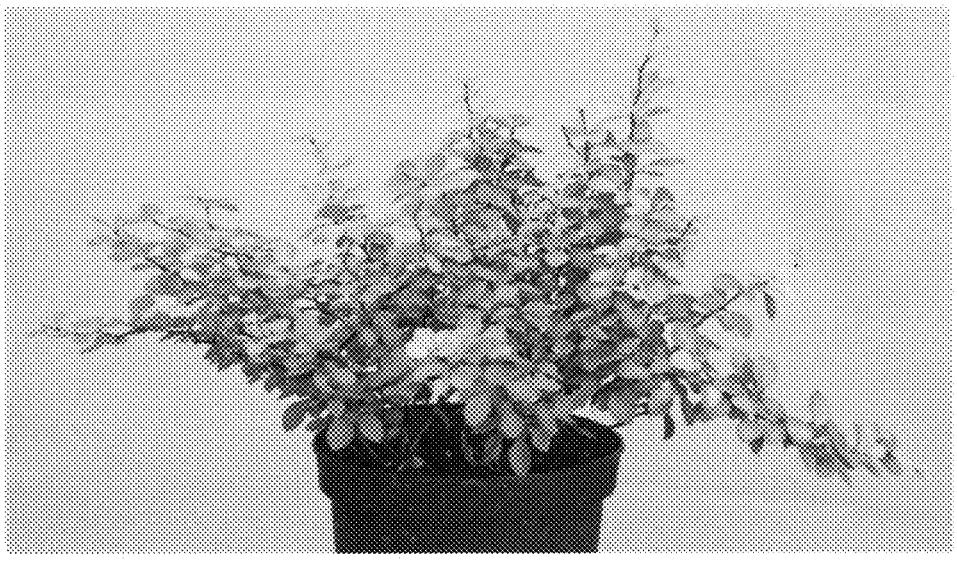
Figure 2:
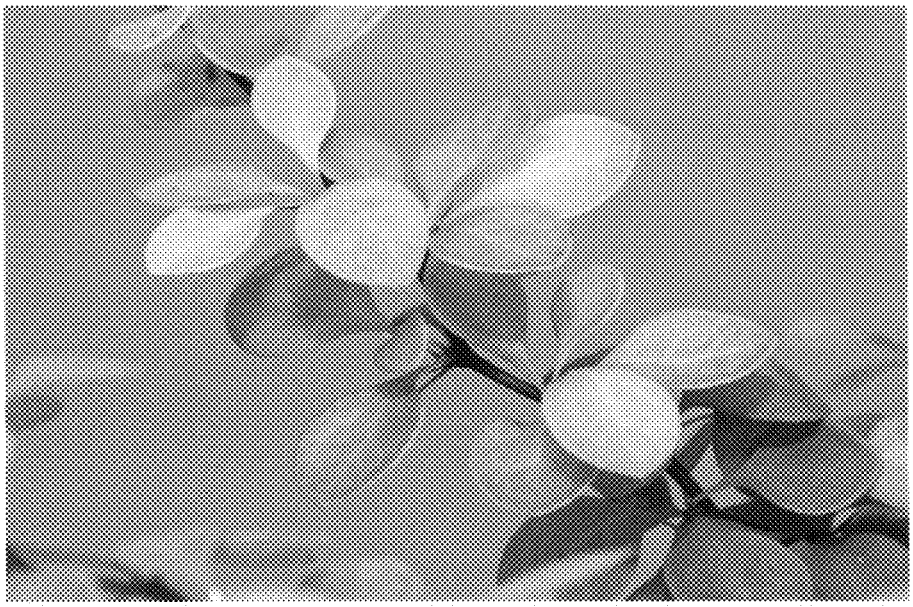

The photograph in FIG. 2 provides a close-up view of the foliage of 'Hoho 2'.

The colors in the photographs may differ slightly from the color values cited in the detailed botanical description, which accurately describe the colors of the new *Berberis*.

DETAILED BOTANICAL DESCRIPTION OF THE PLANT

The following is a detailed description of two-year-old plants of the new cultivar field grown outdoors in 2-liter containers in Zevenaar, The Netherlands. Plants were grown under average day temperatures of 10° to 23° C. and average night temperatures of 1° to 14° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General plant characteristics:

*Plant type.*—Perennial deciduous shrub, flattened broad spreading.

*Plant habit.*—Broad spreading to spreading upright.

*Height and spread.*—Reaches about 24.3 cm in height and 40.5 cm in spread in a 2-liter container and matures to about 75 cm in height and 100 cm in spread.

*Cold hardiness.*—At least in U.S.D.A. Zone 5.

*Disease and pest resistance.*—No susceptibility or resistance to diseases or pest has been observed, however the foliage has been observed to be healthy under the conditions tested and no infections by wheat yellow rust caused by *Puccinia striiformis* has been observed.

*Root description.*—Fibrous, 162B in color with blotches of 163A.

*Growth rate.*—Moderate, about 15 cm in one season on a young plant.

*Propagation.*—Softwood cuttings.

Stem description:

*Stem size.*—Lateral branches are an average of 13.5 cm in length and 1.5 mm in, diameter.

*Stem shape.*—Round.

*Stem color.*—Young shoots; 179A, later turning N170B on upper side, 152D on under side, mature stems; N199C to 200B.

*Stem surface.*—Slightly glossy.

*Stem strength.*—Strong.

*Internode length.*—Average of 1.1 cm.

*Branching habit.*—Moderate to high with an average of 17 lateral branches.

*Branching aspect.*—Lateral branches slightly angled, in an average angle of 40°.

Foliage description:

*Leaf shape.*—Obovate.

*Leaf division.*—Simple.

*Leaf base.*—Long attenuate.

*Leaf apex.*—Broadly acute to abruptly acute.

*Leaf margins.*—Entire.

*Leaf attachment.*—Sessile.

*Leaf arrangement.*—Alternate, clustered.

*Leaf surface.*—Both surfaces are smooth, upper surface is very slightly glossy, lower surface is dull.

*Leaf color.*—Upper surface immature foliage; color between 154B to 1B, lower surface immature foliage; 151D, mature upper surface foliage; N144A, leaves at the base of the branches ("inside" the plant in the shade) 144A, mature lower surface foliage; 145A, leaves at the base of the branches ("inside" the plant in the shade) 139D.

*Leaf number.*—5 per cluster at each node, average of 13 nodes per lateral branch, average of 65 leaves per lateral branch.

*Leaf size.*—Average of 2.4 cm in length and 1.4 cm in width.

*Leaf aspect.*—Held nearly horizontal.

*Leaf fragrance.*—None.

*Leaf veins.*—Pinnate, upper surface color; 144C, shaded leaves at base of branch ("inside" the plant in the shade) 144A, lower surface color; N144A, shaded leaves at base of branch ("inside" the plant in the shade) 144B.

*Petioles.*—Average of 3 mm in length and 1 mm in width, 181A to 181B in color, glabrous surface.

*Thorn.*—Below each node is an average of three very sharp thorns; average length of main thorn is 5 mm, average length of lateral thorn is 4 mm, average width at base for thorns is 1 mm, color; young thorns are 165C to 165D, tip is 200A to 200B, older thorns are 200D, tip is 200A to 200B.

Flower description: No flowers have been observed.

Fruit and seed: Seed production has not been observed.

It is claimed:

1. A new and distinct cultivar of *Berberis* plant named 'Hoho 2' as herein illustrated and described.

* * * * *